(12) United States Patent
Vancamberg et al.

(10) Patent No.: US 11,963,670 B2
(45) Date of Patent: Apr. 23, 2024

(54) SYSTEMS AND METHODS FOR IDENTIFYING BIOPSY LOCATION COORDINATES

(71) Applicant: GE Precision Healthcare LLC, Wauwatosa, WI (US)

(72) Inventors: Laurence Vancamberg, Poissy (FR); Clement Jailin, Antony (FR); Serge Muller, Guyancourt (FR)

(73) Assignee: GE Precision Healthcare LLC, Wauwatosa, WI (US)

( * ) Notice: Subject to any disclaimer, the term of this patent is extended or adjusted under 35 U.S.C. 154(b) by 304 days.

(21) Appl. No.: 17/188,357

(22) Filed: Mar. 1, 2021

(65) Prior Publication Data

US 2022/0273273 A1 Sep. 1, 2022

(51) Int. Cl.
*A61B 10/02* (2006.01)
*A61B 6/00* (2006.01)
(Continued)

(52) U.S. Cl.
CPC ........ *A61B 10/0275* (2013.01); *A61B 6/0414* (2013.01); *A61B 6/40* (2013.01); *A61B 6/4275* (2013.01); *A61B 6/5205* (2013.01); *G06T 7/0012* (2013.01); *G06T 7/73* (2017.01); *G06T 2207/10116* (2013.01); *G06T 2207/20081* (2013.01); *G06T 2207/30068* (2013.01); *G06T 2207/30096* (2013.01)

(58) Field of Classification Search
CPC ............................... G06T 7/0012; G06T 7/73
See application file for complete search history.

(56) References Cited

U.S. PATENT DOCUMENTS

2010/0067769 A1  3/2010  Neemuchwala et al.
2015/0208997 A1*  7/2015  Mahameed ............ A61B 6/502
                                                              600/436
(Continued)

FOREIGN PATENT DOCUMENTS

WO  2006055251 A2  5/2006

OTHER PUBLICATIONS

Cherkezyan, L. et al. Predicting location of breast lesions in supine position from prone MRI data using machine learning, European Society of Radiology, 2019, pp. 1-10.

*Primary Examiner* — Carolyn A Pehlke
(74) *Attorney, Agent, or Firm* — Andrus Intellectual Property Law, LLP

(57) ABSTRACT

A method for determining a lesion location in a patient for biopsy along X, Y, and Z axes. The method includes positioning the patient in an examination device to collect examination images showing the lesion. The method includes positioning the patient in a biopsy device configured for holding the patient during the biopsy and collecting a biopsy image of the patient using the biopsy device. The method includes analyzing the biopsy image to determine a measured x-coordinate and a measured y-coordinate of the lesion along the X and Y axes, respectively, analyzing the examination images to determine a calculated z-coordinate along the Z axis of the lesion, and determining the location of the lesion based on the measured x-coordinate and the measured y-coordinate from the biopsy image and the calculated z-coordinate determined from the one or more examination images.

19 Claims, 8 Drawing Sheets

(51) Int. Cl.
*A61B 6/04* (2006.01)
*A61B 6/40* (2024.01)
*A61B 6/42* (2024.01)
*G06T 7/00* (2017.01)
*G06T 7/73* (2017.01)

(56) References Cited

U.S. PATENT DOCUMENTS

2019/0325573 A1* 10/2019 Bernard ................. A61B 6/469
2020/0311923 A1* 10/2020 Walton ...................... G06T 7/30

* cited by examiner

Prior View 1 (e.g., CC View)

Prior View 2 (e.g., MLO View)

MLO view

SYSTEMS AND METHODS FOR IDENTIFYING BIOPSY LOCATION COORDINATES

FIELD

The present disclosure generally relates to systems and methods for identify location coordinates for performing a biopsy, and more particularly to systems and methods for providing 3D coordinates of a lesion using non-angulating x-ray mammography devices.

BACKGROUND

Screening x-ray mammography has become commonplace as an initial step to detect breast cancer. If suspicious tissue is detected in these screening images, a subsequent biopsy is sometimes required to investigate this suspicious tissue. The initial screening images are collected using an examination device, such as GE Healthcare's® Senographe Crystal or Senographe Pristina. The examination device emits energy or radiation (x-rays) from an x-ray tube towards through the patient's anatomy, which is then detected by an x-ray detector positioned on the opposite side of the anatomy. The examination device then measures the x-ray absorption of the tissues using the x-ray detector and produces an image of the patient's anatomy (in this example the breast). Images are typically collected along multiple views, for example the craniocaudal view, a mediolateral oblique view, and a mediolateral view, according to practices known in the art. In those procedures, the tube and detector rotate together and image the breast in various compressed configurations. A clinician subsequently analyzes the images produced by the examination device at each view to detect any lesions or areas of tissue suspected to have an abnormality.

If the clinician detects any such potential abnormality, a biopsy may be ordered to further investigate samples of the suspect anatomy. The biopsy may be performed with the anatomy positioned in a similar manner to when the screening images were collected with the examination device, but now using a biopsy device configured to perform the biopsy on the same or another mammography system (now referred to as a biopsy system throughout the present disclosure for clarity). An exemplary biopsy device is the GE Healthcare® Senographe Pristina Serena biopsy system.

For the purpose of clarity, the following labels will be used unless otherwise noted or implied:

X,Y,Z: axis of the detector $x_{b-3D}$, $y_{b-3D}$, $z_{b-3D}$: 3D position of the lesion in biopsy configuration $x_{b-2D}$, $y_{b-2D}$: 2D pixel position of the lesion in biopsy configuration 'b' refers to biopsy $x_{i-2D}$, $y_{i-2D}$: 2D pixel position of the lesion in view i $x_{i-3D}$, $y_{i-3D}$ $z_{i-3D}$: 3D voxel position of the lesion in view i 'i index'=number of the view: 0-1-2-3

"Measured" generally refers to being detected in an image or volume, as opposed to being "calculated".

In order to perform the biopsy, the 3D coordinates ($x_{b-3D}$,$y_{b-3D}$,$z_{b-3D}$) of the lesion (labeled with the index 'b' in the biopsy configuration) defined in a coordinate system (X,Y,Z) attached to the detector plane, named detector referential, as the patient is currently positioned, must first be determined such that the clinician knows the proper positioning for the biopsy needle. The X and Y axes are in the plane of the detector while the Z axis is normal to this plane. To determine these 3D coordinates and target the lesion, additional images are collected by the biopsy device, using at least two views of the anatomy at different angles of an x-ray tube relative to the anatomy. In certain devices, known as "angulating devices", the x-ray tube is rotatable relative to the x-ray detector, in other words having an additional degree of freedom (DOF) versus x-ray tubes that are fixed relative to the detector. An exemplary angulating device is GE Healthcare's® Senographe Pristina mammography device. This enables two views of the anatomy to be collected without moving the x-ray detector (and thus without moving the patient) by moving the x-ray tube only (see FIG. 1). For non-angulating biopsy devices, the two views are collected by rotating both the x-ray tube and the x-ray detector together relative to the anatomy, for example rotating 90° or another angle on a gantry (see FIGS. 2A-2B).

If the lesion is located using the projection images, the 2D pixels coordinates where the lesion is located in the ith X-ray images are then combined with the knowledge of the biopsy device geometry to deduce the 3D coordinates of the lesion ($x_{b-3D}$,$y_{b-3D}$,$z_{b-3D}$) in the biopsy compressed configuration in the detector referential (X,Y,Z). If the lesion is located using a reconstructed 3D volume, the slice containing the lesion and the pixel of this slice where the lesion is located are used to deduce the 3D coordinates of the lesion in the detector referential.

Once the ($x_{b-3D}$,$y_{b-3D}$,$z_{b-3D}$) coordinates of the lesion in the detector referential are obtained they can be transformed into other referential in order to proceed to the biopsy, for example they can be transformed into a biopsy robot referential, or an exam room referential. Once the 3D coordinates of the lesion are computed using techniques presently known in the art, the biopsy may be performed, again using methods presently known in the art.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

One embodiment of the present disclosure generally relates to a method for determining a location of a lesion for biopsy in a patient along X, Y, and Z axes of a referential attached to the detector. The method includes positioning the patient in an examination device and collecting one or more examination images of the patient using the examination device, where the one or more examination images show the lesion. The method includes positioning the patient in a biopsy device configured for holding the patient during the biopsy and collecting a biopsy image of the patient using the biopsy device, where the biopsy image shows the lesion. The method includes analyzing the biopsy image to determine a measured x-coordinate and a measured y-coordinate of the lesion along the X and Y axes, respectively, and analyzing the one or more examination images to determine a calculated z-coordinate of the lesion along the Z axis. The method includes determining the location of the lesion along the X, Y, and Z axes based on the measured x-coordinate and the measured y-coordinate from the biopsy image and the calculated z-coordinate determined from the one or more examination images.

In certain embodiments, the calculated z-coordinate is determined from analysis of the one or more examination images.

In certain embodiments, the method further comprises acquiring additional parameters other than from the biopsy image and the one or more examination images, and further comprising including the additional parameters in the analysis of the one or more examination images to determine the calculated z-coordinate of the lesion.

In certain embodiments, the one or more examination images include a first examination image taken in a craniocaudal view and a second examination image taken in one of a mediolateral oblique view and a mediolateral view.

In certain embodiments, the biopsy of the lesion is performed at the location determined by inserting, non-parallel to the Z axes, a needle into the patient.

In certain embodiments, the biopsy image analyzed is exactly one biopsy image, and the exactly one biopsy image is the only image collected of the patient while the patient is positioned in the biopsy device that is analyzed when determining the location of the lesion.

In certain embodiments, the biopsy device includes an x-ray tube and an x-ray detector opposite the x-ray tube, where the biopsy image is collected only when the x-ray detector is positioned below the lesion.

In certain embodiments, the x-ray tube of the biopsy device is non-angulating.

In certain embodiments, the method includes analyzing the one or more examination images to determine the calculated z-coordinate of the lesion includes identifying one or more landmarks in at least one of the biopsy image and in the one or more examination images.

In certain embodiments, the calculated $z_{b\text{-}3D}$-coordinate is determined based on distances between the landmark and the lesion.

In certain embodiments, the method includes dividing the one or more examination images into segments, where analyzing the one or more examination images to determine the calculated z-coordinate of the lesion includes identifying which one of the segments the lesion is located in.

In certain embodiments, the segments are divided as layers between a top and a bottom of the patient stacked along the Z-axis, and the calculated z-coordinate of the location of the lesion is determined based on the one of the segments identified to have the lesion in the one or more examination images.

In certain embodiments, the biopsy is performable using a needle that extends along a longitudinal axis between a tip and a handle, where the needle defines a notch therein, where the notch has a notch height parallel to the longitudinal axis and the segments have segments heights along the Z-axis, and where the notch height is at most equal to the segment heights.

In certain embodiments, the segments include five segments of equal height along the Z-axis.

In certain embodiments, the method includes determining a morphology change to the patient caused by the patient being positioned in the examination device, determining the calculated z coordinate of the lesion includes analyzing effects of the morphology change in the one or more examination images.

In certain embodiments, the segments have segments heights along the Z-axis, where the segment heights are based at least in part on the morphological change determination.

In certain embodiments, at least one of deep learning and artificial intelligence is used for at least one of analyzing the biopsy image to determine the measured x-coordinate and the measured y-coordinate, analyzing the one or more examination images to determine the calculated z-coordinate, and determining the location of the lesion based on the measured x-coordinate, the measured y-coordinate, and the calculated z-coordinate.

In certain embodiments, the method further comprises providing training examination images and known z-coordinates of training lesions corresponding thereto to train the at least one of the deep learning and the artificial intelligence.

In certain embodiments, at least one of the deep learning and the artificial intelligence applies a biomechanical model.

Another embodiment according to the present disclosure generally relates to a system for collecting a biopsy of a lesion within a patient based on one or more examination images previously collected from an examination device, where the lesion has a location along X, Y, and Z axes. The system includes an x-ray tube configured to emit energy towards the patient and an x-ray detector opposite the x-ray tube, where the x-ray detector is configured to detect the energy emitted towards the patient after passing through the patient. A compression paddle defines a biopsy window therein and is configured to compress the patient between the compression paddle and the x-ray detector while the energy is emitted from the x-ray tube and detected by the x-ray detector. A processing system communicates with the memory system and the x-ray detector, where the processing system is configured to: generate a biopsy image of the patient based on the energy detected by the x-ray detector, wherein the biopsy image includes the lesion; access the one or more examination images of the patient previously collected using the examination device, wherein the one or more examination images include the lesion; analyze, while the patient remains compressed between the compression paddle and the x-ray detector, the biopsy image to determine a measured x-coordinate and a measured y-coordinate of the lesion along the X and Y axes, respectively; analyze the one or more examination images to determine a calculated z-coordinate of the lesion along the Z axis; and determine the location of the lesion based on the measured x-coordinate and the measured y-coordinate from the biopsy image and the calculated z-coordinate from the one or more examination images. The system is configured for the biopsy of the lesion while the patient remains compressed between the compression paddle and the x-ray detector.

Various other features, objects and advantages of the disclosure will be made apparent from the following description taken together with the drawings.

BRIEF DESCRIPTION OF THE DRAWINGS

The present disclosure is described with reference to the following Figures.

DETAILED DISCLOSURE

Figure 1:
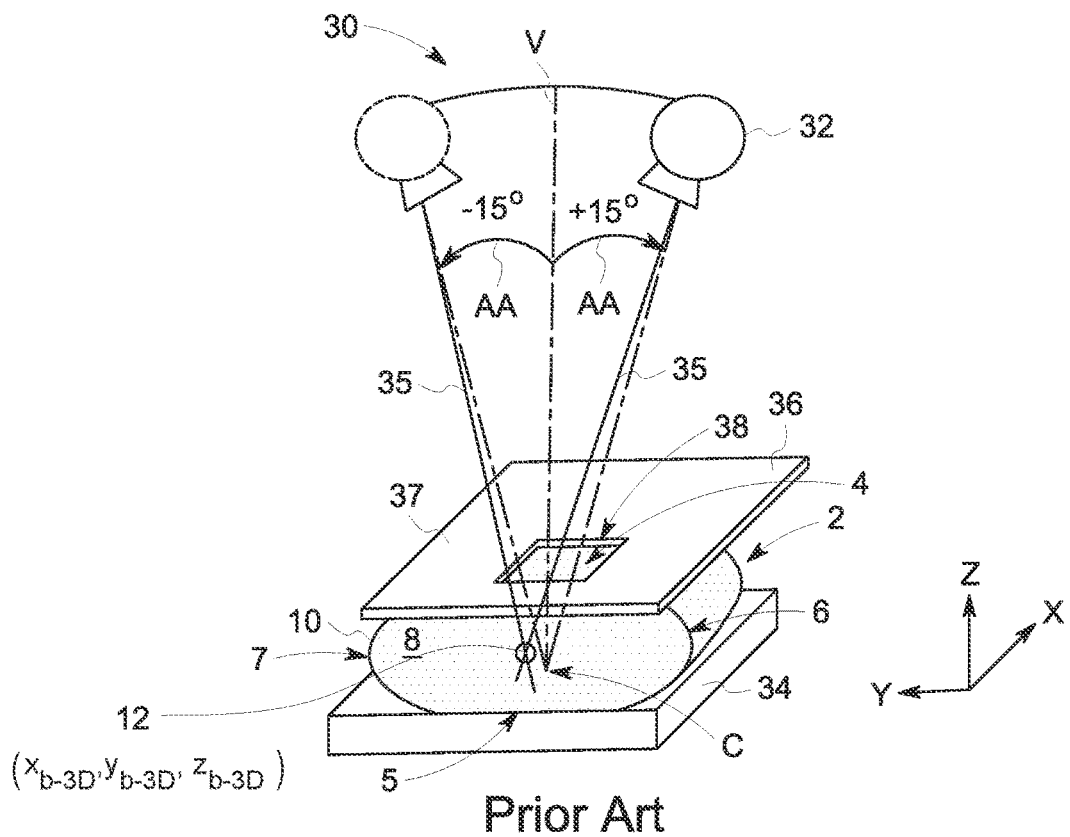
FIG. 1 depicts an exemplary isometric view of a biopsy device as presently known in the art.

As described in the BACKGROUND above, FIG. 1 depicts an exemplary biopsy device with angulation as presently known in the art. As shown, the biopsy device 30 is configured for performing a biopsy on a patient, or the patient's anatomy 2 (shown here as a breast). The anatomy 2 extends between a top 4 and bottom 5, left 6 and right 7, and front 8 and back (not shown). The anatomy 2 is shown compressed between a biopsy compression paddle 36 and an x-ray detector 34 as presently known in the art. A top surface 37 of the compression paddle 36 is positioned facing the x-ray tube 32, with a lower surface (not numbered) against the anatomy 2. A lesion 12 is shown within the anatomy 2, aligned to be imaged using an x-ray tube 32 projecting a cone-shaped beam 33 (see FIG. 2A) comprising individual beam lines 35 the anatomy 2 to be detected by the x-ray detector 34. A biopsy window 38 is defined through the compression paddle 36, through which a clinician may perform a biopsy of the lesion 12.

The biopsy device 30 shown is configured to provide rotational degrees of freedom (DOF) such that the x-ray tube 32 is angulating, meaning that the x-ray tube 32 may be rotated relative to the position of both the anatomy 2 and the x-ray detector 34. In the present case, the x-ray tube 32 rotates between angulation angles AA and -AA on either side of the vertical axis V.

By capturing images at angulation angles AA +15° and −15°, for example, and combining knowledge of the specific geometry of the biopsy device 30, coordinates of the lesion 12 can be deduced in all 3 axes (X,Y,Z) according to methods presently known in the art. The X,Y,Z axes are defined from respectively being the axis of the image plane and the axis orthogonal to this plane. Based on these 3D coordinates, a biopsy of the lesion 12 may then be performed by convention methods. It will be recognized that alternative angulation angles AA are also possible and need not be centered above the vertical axis V (here coinciding with the Z axis).

However, the inventors have recognized that many biopsy devices 30 do not provide angulation of the x-ray tube 32, whereby angulation increases the complexity and expense of these devices such that smaller facilities or lower income regions often cannot afford them. In these cases, clinicians use a simpler, non-angulating biopsy device 30 such as shown in FIGS. 2A and 2B in a manner to identify the 3D location of the lesion by an alternative method.

Figure 2A:
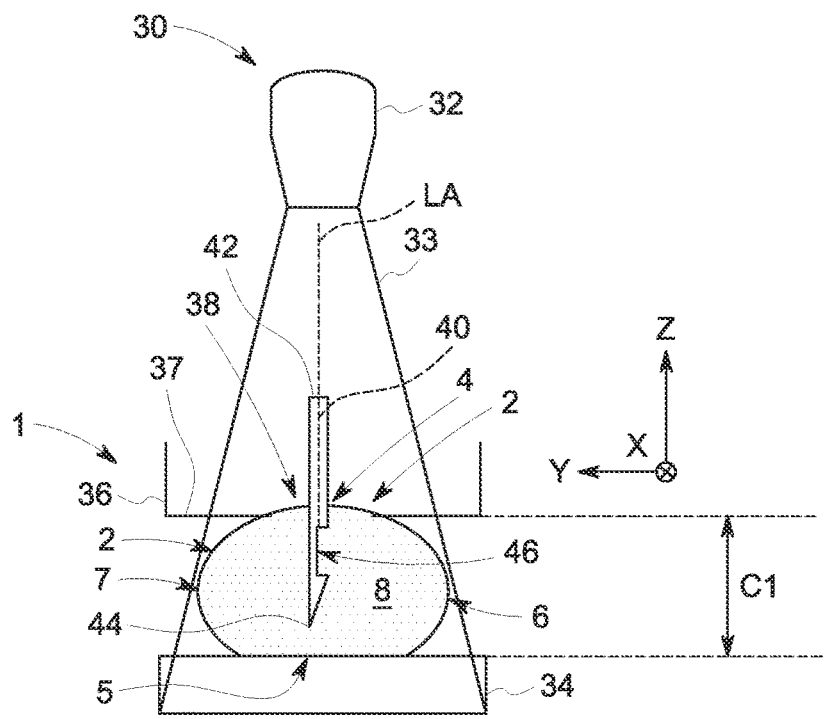
FIGS. 2A and 2B depict a front view of an alternate biopsy device presently known in the art with the x-ray tube and x-ray detector rotated together.

As shown in FIG. 2A, a first image is collected via a non-angulating biopsy device 30 with the x-ray tube 32 centered above the anatomy 2, once again with the anatomy compressed between the compression paddle 36 and the x-ray detector 34 as was the case during the initial screening using an examination device. For the purpose of disclosure, the examination device may be the model provided in the BACKGROUND above and may be considered to be the same device shown in FIG. 1 or 2A as the biopsy device 30 (but used ahead of time, before compressing the patient for conducting the biopsy, for example). However, in contrast to the angulating biopsy device 30 of FIG. 1, the technique of FIGS. 2A-2B require to perform a second image with the biopsy needle 40 positioned within the anatomy 2 during this imaging process before the biopsy sampling is conducted. The needle 40 presently shown is of the type presently known in the art, extending along a longitudinal axis LA between a handle 42 and a tip 44 with a notch 46 defined therebetween. The notch 46 is configured to extract the biopsy sample from the anatomy 2 while the anatomy 2 remains compressed between the compression paddle 36 and the x-ray detector 34, presently at compression 1 C1.

Figure 2B:
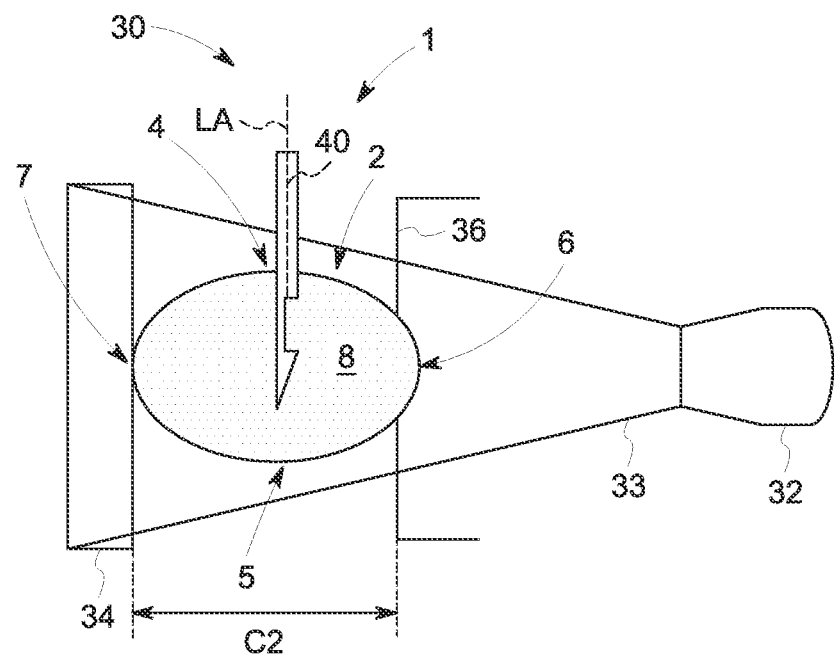

Once images are collected with the biopsy device 30 positioned as shown in FIG. 2A, a third image is collected with the biopsy device 30 configured as shown in FIG. 2B, in this example with the x-ray tube 32 and x-ray detector 34 rotated 90° relative to the anatomy 2 (here corresponding to a mediolateral (ML) view). In this case, the biopsy needle 40 remains positioned within the anatomy 2, which is subsequently compressed between the compression paddle 36 and the x-ray detector 34 at a compression 2 C2. As will be recognized, information relating to the location of the lesion 12 within the anatomy 2 may be obtained along the X and Y axes with the biopsy device 30 configured as shown in FIG. 2A, based on the location detected on the x-ray detector 34. However, as exemplified in FIG. 3, no information may be obtained from the x-ray detector 34 with respect to the location of the lesion within the Z direction, as an infinite number of z locations within the anatomy 2 can produce the same detection location on the x-ray detector 34 in this configuration (i.e., any z location along the line segment 17). For this reason, the second image is collected with the configuration shown in FIG. 2B, which then provides depth location information for the lesion, collectively providing information for all three coordinates.

However, the inventors have recognized that for this method, also known as a 2D lesion location exam, decompressing and recompressing the anatomy 2 while the needle 40 is inserted requires very sensitive manipulation that takes time and is uncomfortable or even painful for the patient. Through experimentation and development, the inventors have created the presently disclosed systems and methods for determining the 3D location of a lesion within patient anatomy using only a single view collected by the biopsy device 30 (for example, as shown in FIG. 2A), but without the need to perform any image with the biopsy needle 40 inserted in the anatomy 2 in the process. In particular, the inventors have recognized that the images collected from previous exams (i.e., those collected during an initial screening by an examination device) may be analyzed and manipulated to estimate or determine the missing Z-axis location of the lesion on the biopsy device. This allows the inventors to identify the 3D location of the lesion for biopsy while eliminating the need to rotate the x-ray tube 32 while the patient is positioned in the biopsy device 30, eliminating the need to capture another image while the patient is positioned in the biopsy device 30, and eliminating the need for the needle 40 to be inserted other than for the actual performance of the biopsy.

Figure 3:
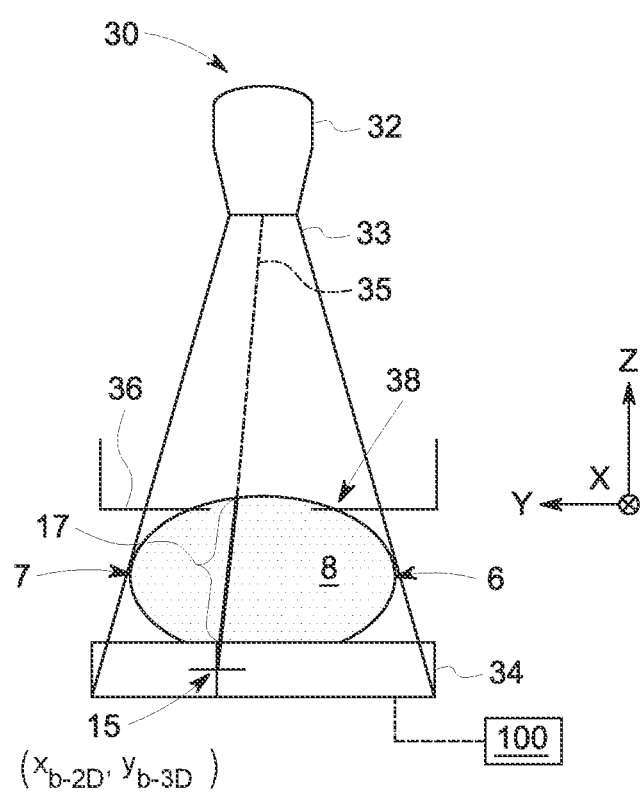
FIG. 3 is a front view of a biopsy device according to the present disclosure, depicting a line of lesion possibilities as detected by one or more images from the x-ray detector.

FIG. 3 depicts a biopsy device 30 configured for collecting an image of the anatomy 2 similar to that previously discussed, whereby the biopsy device 30 is non-angulating and thus of the more basic form. The image collected with the biopsy device 30 when positioned as shown in FIG. 3 only provides information for the lesion 12 location along the X and Y axes as a function of the z coordinate, which would show up in the x-ray detector 34 as a single point or region as the detected region 15. As such, since no $z_{b-3D}$-coordinate can be derived from this image, the location of the lesion 12 within the anatomy 2 can only be narrowed to existing along a line of lesion possibilities 17 that aligns with the detected region 15 on the x-ray detector 34 (in other words, a line of locations all corresponding to the same projected coordinates of the lesion on the x-ray detector 34).

Figure 4A:
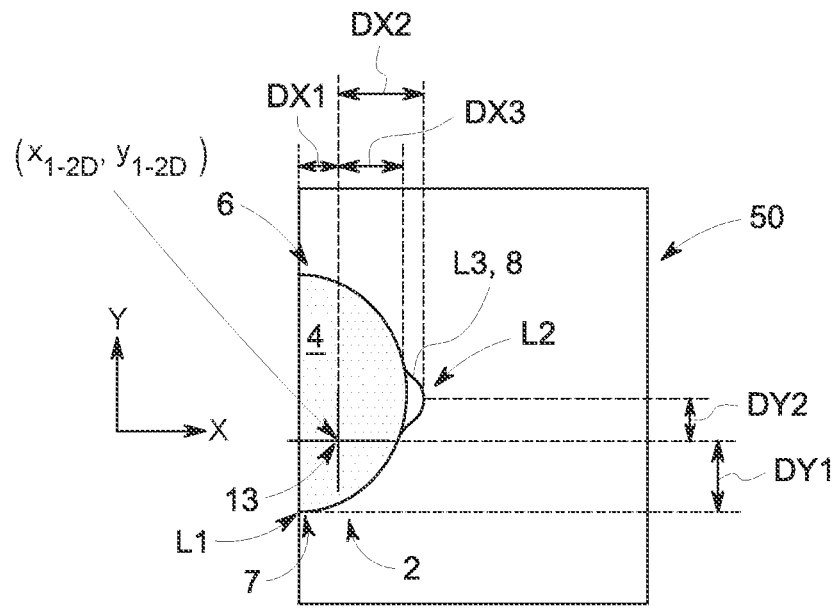
FIGS. 4A-4C depict exemplary images collected using an examination device and applied according to the present disclosure to identify the 3D location of the lesion along the line of lesion possibilities shown in FIG. 3.
Figure 4B:
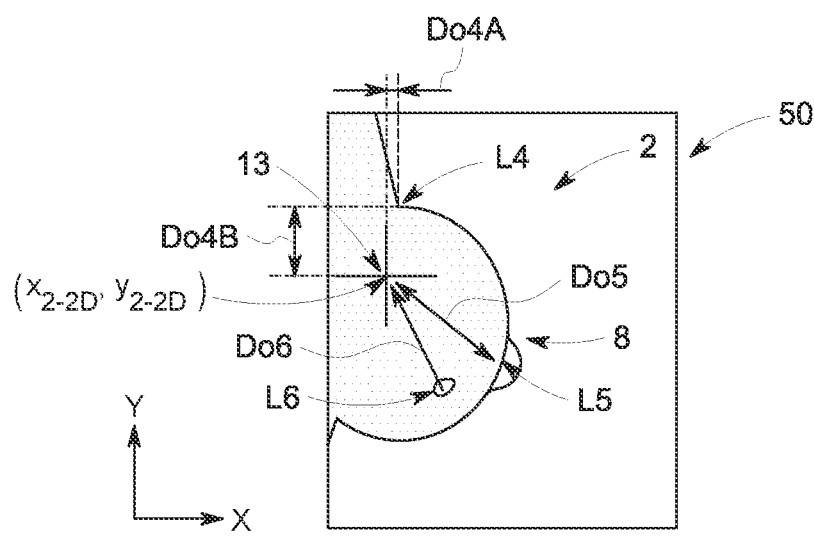
Figure 4C:
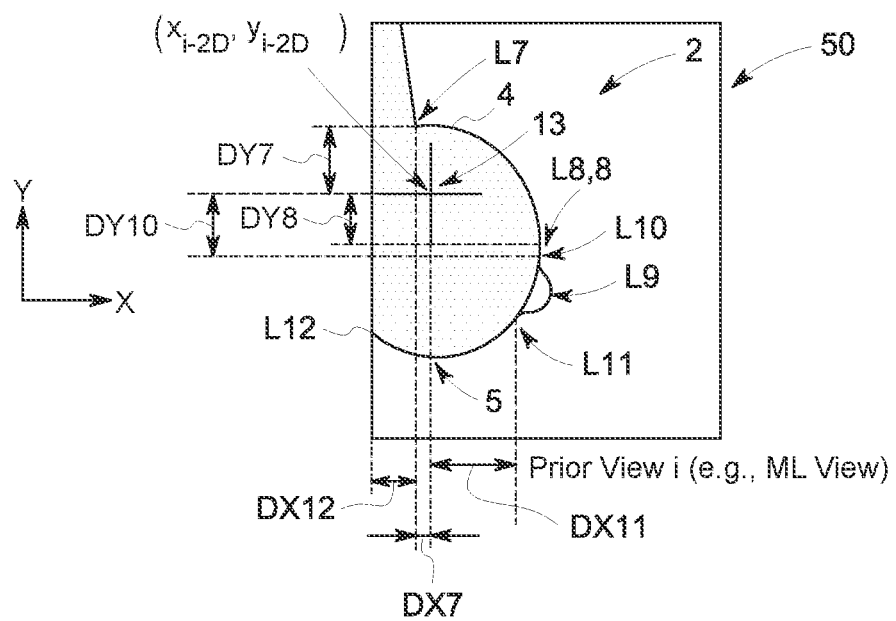

To determine the missing $z_{b-3D}$ components of the lesion 12, the inventors have recognized that images from the prior exams may be analyzed and re-used for a new purpose distinct from that presently known in the art. FIGS. 4A-4C depict images 50 collected at three different views of the anatomy 2, in this case taken along a craniocaudal view, a mediolateral oblique view, and a mediolateral view, respectively, as customarily obtained during screening procedures. Images 50 may be from a 2D mammographic exam, but it will be recognized that 3D reconstructed volumes (3D exams) could also or alternatively be used. It will be also recognized that other views may also be used, and those described above are merely exemplary. In each of the three images 50 shown in FIGS. 4A-4C, the lesion corresponds to image lesion location 13. As will be recognized, the craniocaudal view of the image 50 in FIG. 4A can then be used for determining the image lesion location 13 in the X and Y axes of the image, as well as in the mediolateral view of FIG. 4C. Information may also be obtained from the mediolateral oblique view of FIG. 4B or other views by knowing the angular positioning of the x-ray tube 32 relative to the x-ray detector 34.

Once the image lesion location 13 is identified in the images 50, which may be detected manually by the clinician and/or using automated image analysis techniques known in the art, $(x_{i-2D}, y_{i-2D})$ coordinates of the lesion projection 13 (2D exam) or $(x_{i-3D}, y_{i-3D}, z_{i-3D})$ coordinates for the lesion location (3D exam) may be determined. It should be recognized that the $x_{b-3D}$, $y_{b-3D}$, and $z_{b-3D}$ coordinates of the lesion 12 is solved as a function of the combined coordinate information from the images 50 captured by the x-ray detector 34, based on the positioning of the x-ray tube 32 and x-ray detector 34 and the patient positioning when each image 50 is captured. In other words, every image is initially measured to have a measured x-coordinate and a measured y-coordinate on the x-ray detector 34; however, the x-ray detector 34 itself is not always positioned at the same rotation angle and the patient position may vary. As such, measured $x_{1-2D}$ and $y_{1-2D}$ coordinates or measured $(x_{i-3D}, y_{1-3D}, z_{1-3D})$ if it is a 3D exam may be acquired via the x-ray detector 34 in a first (labeled '1') of the images 50, measured $x_{2-2D}$ and $y_{2-2D}$ coordinates or measured $(x_{2-3D}, y_{2-3D}, z_{2-3D})$ if it is a 3D exam in a second (labeled '2') of the images 50 taken with the x-ray tube 32 in another position, and so on through measured $x_{i-2D}$ and $y_{i-2D}$ or measured $(x_{i-3D}, y_{i-3D}, z_{i-3D})$ if it is a 3D exam with the x-ray detector 34 in an i-th image (labeled 'i') of the images 50 taken in another position.

Additional parameters corresponding to the geometric, mechanical, and/or physical configuration and/or orientation of the acquisition device and/or biopsy device may also be analyzed (collectively referred to as parameters P). These additional parameters provide information other than what is measurable in the images. For example, these additional parameters P may include a compression force by the compression paddles 36, a type of the compression paddles 36 being used (e.g., shapes and sizes of openings therethrough), and/or a measured breast height (e.g., between the compression paddle 36 and the x-ray detector 34) and or a patient related information (e.g. position: sitting/recumbent or view name). In certain examples, some or all of these additional parameters are already provided by the acquisition devices as known in the art. Thus, the $z_{b-3D}$ coordinate of the lesion 12 can be solved as a function of $F(\{x_{i-3D}, y_{i-3D}, z_{i-3D}\}, \{x_{i-2D}, y_{i-2D}\}, P)$.

In certain examples, one or more landmarks (exemplified as landmarks L1-L12 in FIGS. 4A-4C, which may be present in other FIGS.) may be identified within the images 50. By identifying landmarks that are also present in images 50 for multiple views, the landmarks may be used for comparison to the image lesion location 13 to help locality the lesion 12. These landmarks may be external features and/or internal features of the anatomy 2, as will become apparent. For example, FIG. 4A shows landmark 1 L1 defined as the right-most point 7 of the anatomy 2, landmark 2 L2 the nipple or a portion thereof, and landmark 3 L3 the front 8 of the anatomy 2 (excluding landmark 2 L2), which could also be considered as the base of the landmark 2 L2. In this example, distances between the image lesion location 13 and one or more of the landmarks may be measured, for example in first X distance DX1 between the image lesion location 13 and landmark 1 L1, second X distance DX2 between the image lesion location 13 and the second landmark L2, and/or a third X distance DX3 between the image lesion location 13 and landmark 3 L3. Likewise, FIG. 4A may be analyzed to determine one or more measurements in the Y direction, such as first Y distance DY1 between the image lesion location 13 and landmark 1 L1, and/or second Y distance DY2 between the image lesion location 13 and landmark 2 L2, for example.

It will be recognized that additional landmarks L4-L12 with corresponding distances to the image lesion location 13 may also be used in the various views, such as those shown in FIGS. 4B and 4C. These include, for example, the top-most portion of the nipple L10, a central point or edge of a tissue region L6 (characterized as being adipose and/or glandular tissue, for example), and the point at which the anatomy 2 contacts the chest wall under the breast at landmark 12 L12. For example, seventh Y distance DY7 and eighth Y distance DY8 are shown in FIG. 4c as distance along the Y axis from the image lesion location 13 and landmark 7 L7 (e.g., the top of the breast) and landmark 8 L8 (e.g., a vertical midpoint of the breast), respectively. Another exemplary measurement in FIG. 4c is tenth Y distance DY10 between the image lesion location 13 and landmark 10 L10 (e.g., the top of the nipple).

Once again, as shown for the mediolateral oblique view of FIG. 4B, additional information regarding the positioning of the x-ray tube 32 relative to the x-ray detector 34 and patient positioning may be used to determine $x_{b-3D}$, $y_{b-3D}$, and/or $z_{b-3D}$ coordinates in the biopsy configuration. For example, FIG. 4B shows the examples of a fifth oblique distance DOB5 between the image lesion location 13 and landmark 5 L5 (here, defined as the lower-most portion of the anatomy 2).

Figure 6:
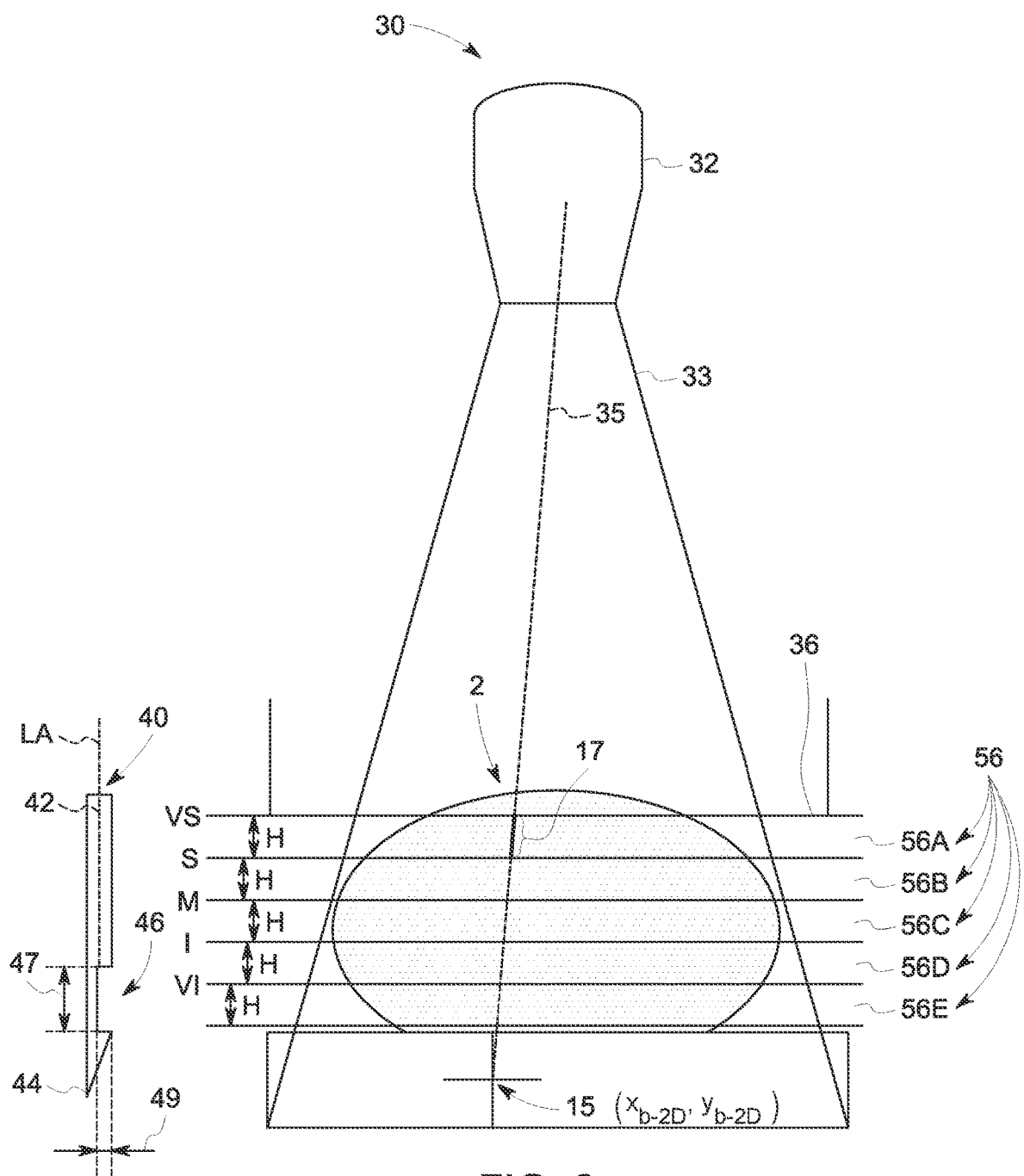
FIG. 6 depicts the biopsy device of FIG. 3, now incorporating the additional information gathered from the images of FIGS. 4A-4C, and/or FIGS. 5A and 5B according to the present disclosure to identify the 3D location the lesion along the line of lesion possibilities for biopsy.
Figure 8:
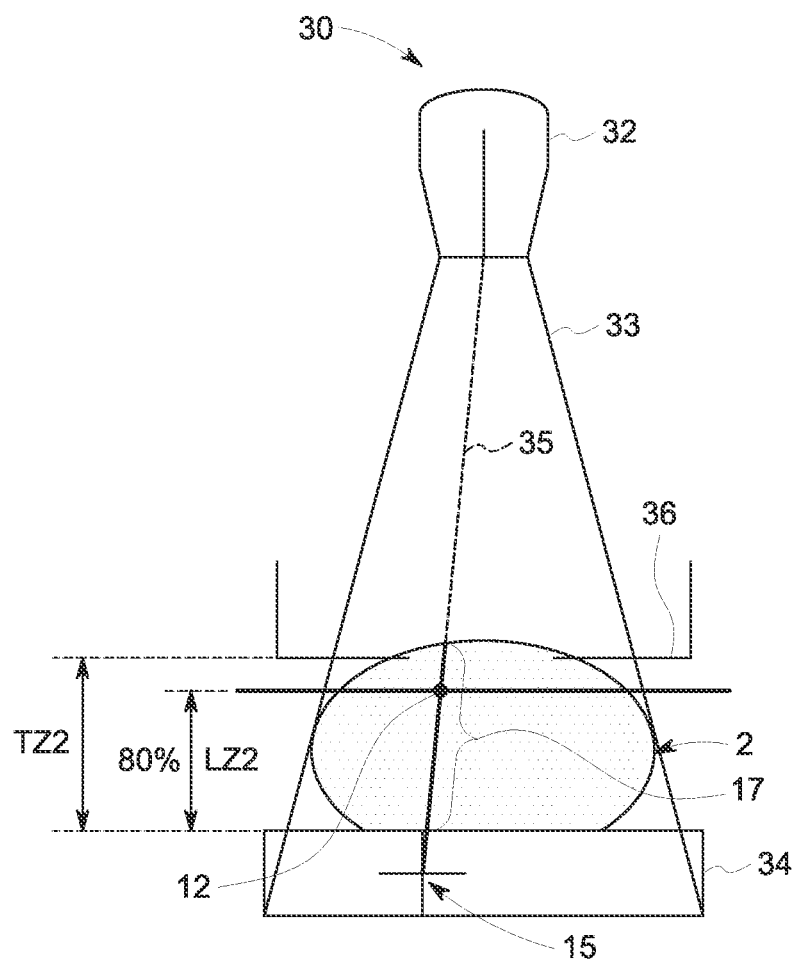
FIG. 8 depicts the biopsy device of FIG. 3 now incorporating the additional information gathered from the images of FIGS. 4A-4C, and/or FIG. 7 and/or the biopsy system to identify the 3D location the lesion along the line of lesion possibilities for biopsy.

In this manner, the previous images from the examination device are used to determined measured coordinates of the image lesion location 13. As discussed above, new, actual coordinates in the X and Y axes can be determined for the lesion 12 within the anatomy 2 as it is positioned in the biopsy device 30 by obtaining an image with the biopsy device 30 configured as shown in FIG. 3, for example. This information from the prior examination images can then be used to deduce the 3D coordinates for the lesion 12 as positioned in the biopsy device 30. As discussed above, the $z_{b-3D}$-coordinate is calculated as a function of the combined coordinate information measured from the images 50, based on the positioning of the x-ray tube 32 and x-ray detector 34 when each image 50 is captured as well as patient positioning information. As shown in FIGS. 6 and 8, this process therefore reduces the length of the line segment 17 from FIG. 3, in certain examples down to a single point. By providing this missing information in the Z direction, the biopsy can then be performed with only the single image collected from the biopsy device 30.

Figure 5A:
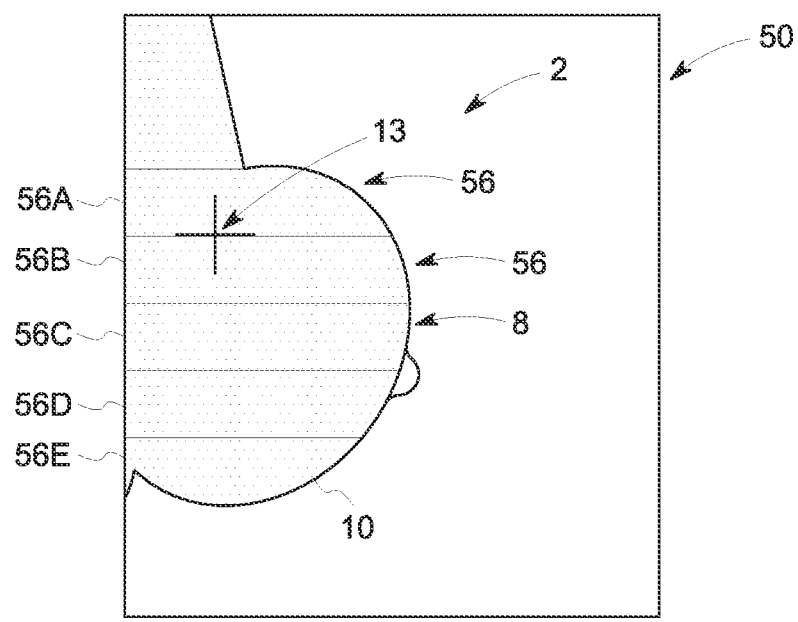
FIGS. 5A and 5B depict exemplary images collected from an examination device similar to that shown in FIG. 4B, now segmented according to the present disclosure for identifying the 3D location of the lesion.
Figure 5B:
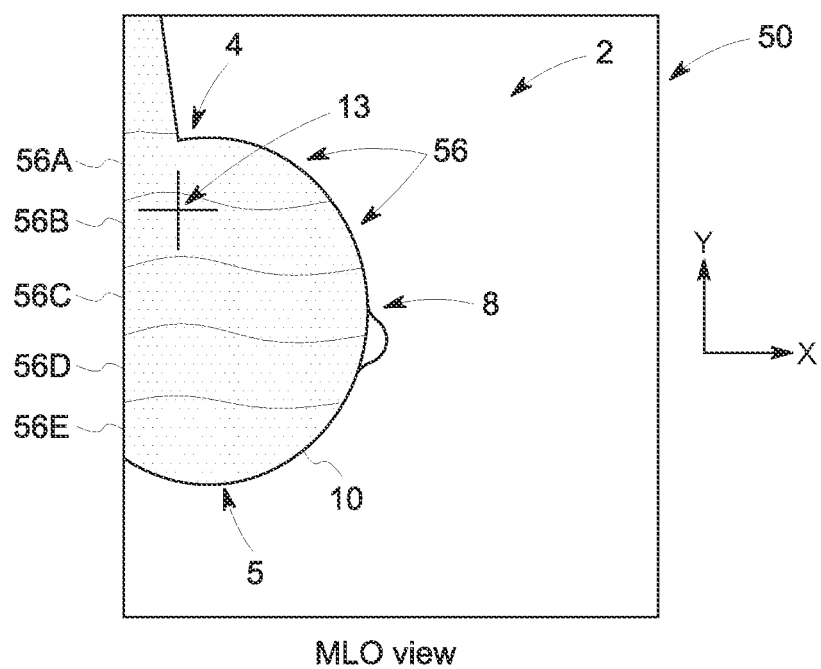

FIGS. 5A-6 depict two processes for determining the measured $x_{i-2D}$ and $y_{i-2D}$ coordinates of the image lesion location 13 as detected on the x-ray detector 34, and consequently translating this to a calculated $z_{b-3D}$ coordinate of the lesion 12 as it is positioned in the biopsy device 30. In this example, the anatomy 2 depicted in the images 50 of FIGS. 5A and 5B are divided into segments 56, in the present examples, segments 56A-56E. In the example of FIG. 5A, these segments 56A-56E are five, equally spaced from horizontal sections. However, it will be recognized that differing numbers of segments 56 may be used, and that such segments 56 need not be equally sized. It is also possible that the segments 56 may be provided in multiple directions, for example with another set running perpendicularly to segments 56A-56E as shown, for example.

By dividing the anatomy 2 of the image 50 into the segments 56A-56E, a clinician may easily discern which of these segments the lesion in image lesion location 13 is located within, in the present example of FIG. 5A within the first segment 56A. Similar segmentation may be provided in multiple views to collectively discern with high accuracy the 3D coordinates of the lesion 12. As shown in FIG. 6, the line segment 17 previously shown in FIG. 3 known from the single biopsy device 30 image alone can thus shortened, now corresponding with the segment height H of each of the five segments 56A-56E (in this case corresponding to the first segment 56A). These segments may also be labeled more descriptively to assist in the clinician's analysis process, for example labeled as very superior (VS), superior (S), middle (M), inferior (I), and very inferior (VI) locations of the anatomy 2 as segmented.

It will be recognized that these segments 56 essentially serve as the landmarks for comparison, which may be used alone or in conjunction with the comparisons to landmarks L1-L12 discussed above.

The inventors have recognized that it is particularly advantageous for the segment heights H to be less than or equal to the sample size of the anatomy 2 collected by the needle 40 during the biopsy to ensure that the entire possibility of lesion locations in the Z axis is collected for analysis. FIG. 6 depicts an exemplary needle 40 defining a notch 46 therein for obtaining the sample from the anatomy 2. The notch 46 has a height 47 along the longitudinal axis LA of the needle 40, and a depth 49 recessing into the needle 40. In this manner, the number of segments 56 for dividing the anatomy 2 in the images 50 may be optimally chosen such that the segment heights H thereof are less than the height 47 of the notch 46 in the needle 40. This ensures that the entire range of anatomy 2 identified as corresponding to the lesion 12 is collected during the biopsy, avoiding false-negatives and/or repeated biopsy procedures.

More generally, the inventors have recognized that it is particularly advantageous when the biopsy is performed using a needle inserted following a certain direction if the uncertainty of the lesion location along X,Y,Z is inferior to the projection of the needle notch along these X,Y,Z axis.

As shown in the image 50 of FIG. 5B, the segments 56 need not be equal and need not be linear. For example, the inventors have recognized that the outer surface or shape 10 of the anatomy 2 changes based upon the compression thereof and the relative positioning of the compression paddle to the anatomy 2. Moreover, the morphology of the shape 10 of the anatomy 2 depends not only on the amount of compression by the compression paddle 36, but also based on the original shape 10 of the anatomy 2 to begin with. Size, contour, density, and distribution of the anatomy 2 all play a factor in how the anatomy 2 will response under compression, including the particular distribution and concentration of adipose and glandular tissue within the anatomy 2, for example.

Figure 7:
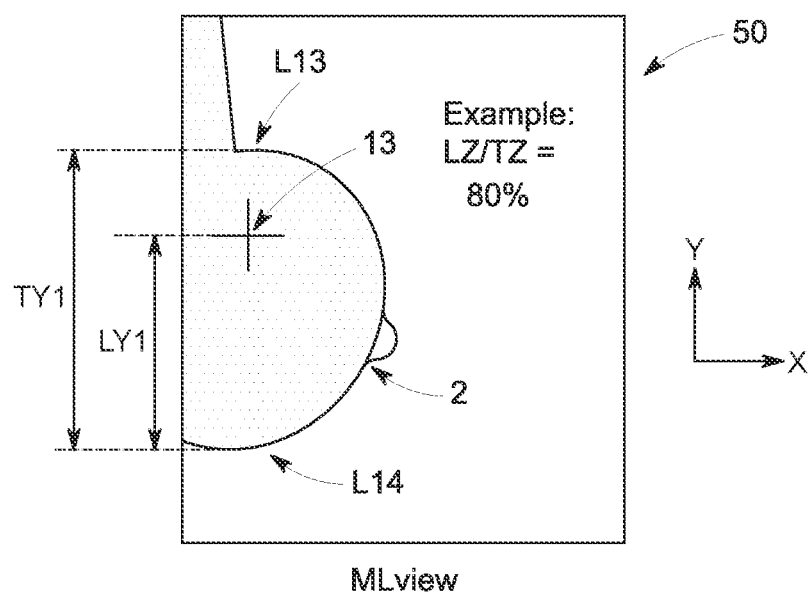
FIG. 7 depicts an alternative method for identifying the 3D location of the lesion according to the present disclosure using an image similar to that shown in FIG. 4C.

An alternative process is shown in FIGS. 7 and 8. In this example, landmark 13 L13 is defined as the uppermost portion of the anatomy 2, and landmark 14 L14 as the lowermost portion of the anatomy, each as depicted in the image 50 collected in the mediolateral (ML) view. A first total measurement TY1 in Z axis is determined between the landmark 13 L13 and landmark 14 L14 to define 100% of the height of the anatomy 2 in the Z axis. A first lesion measurement LY1 in the Z axis is also measured between landmark 14 L14 and the image lesion location 13. These values can then be compared (here divided) to determine the image lesion location 13 relative to the total height of the anatomy 2 as a percentage, in this example approximately 80% to the top designated as landmark 13 L13. This value may then be used, in certain examples corrected based on any morphological changes to the shape 10 between the images 50 collected from the examination device to the biopsy device 30 as shown in FIG. 8, to again determine an calculated $z_{b-3D}$ coordinate of the lesion 12 that is more specific than the line segment 17 provided by the single image captured by the biopsy device 30 alone.

Specifically, a second total Z measurement TZ2 is measured based on the image collected by the biopsy device 30 between the uppermost and lowermost portions of the anatomy 2 (using the same landmark 13 L13 and landmark 14 L14 from above). Assuming the same ratio of the height determined via the image 50 in FIG. 7 may be applied (in other words, no correction for morphological changes to the shape 10) the location of the lesion 12 would again be 80% of the height of the second total Z height TZ2, here essentially the measurement between the compression paddle 36 and the x-ray detector 34. The actual or calculated $z_{b-3D}$ coordinate of the lesion 12 would then by 80% times the second total Z height TZ2, as shown in FIG. 8.

Accordingly, as shown in FIG. 5B, the segments 56 may be defined through biomechanical modeling to account for the morphological impacts on the shape 10 of the anatomy 2 as captured in the image 50, thus being correctable to the specific shape 10 of the anatomy 2 when later applied to the single image of the anatomy 2 as positioned in the biopsy device 30, for example as shown in FIG. 6. This modeling may be based on the geometrical characteristics of shape 10 of the anatomy 2, based on biomechanical properties of the breast tissues, and/or determinations made from the images 50 from the examination device, for example.

In certain examples, a regression model (e.g., linear regression models, neural networks, regression trees, etc.) is used that can learn the geometric mapping transformation between views and between the different 3D compressed geometries. For example, Multi-layer Perceptron may be used as a type of regression modeling, which is known in the art. This technique allows relating any measured $x_{i-2D}$-coordinate and the measured $y_{i-2D}$-coordinate in the one or more examination images to the $z_{b-3D}$-coordinate of the lesion in the biopsy image. In certain examples, artificial intelligence techniques such as deep learning, and/or machine learning techniques may be employed (alone or in combination with traditional image analysis techniques and biomechanical modeling) to determine the $x_{b-3D}$, $y_{b-3D}$, and $z_{b-3D}$ coordinates of the lesion 12 from the measured coordinates of the image lesion location 13. For example, the data may be analyzed using TensorFlow™ or other commercially available platforms.

Figure 9:
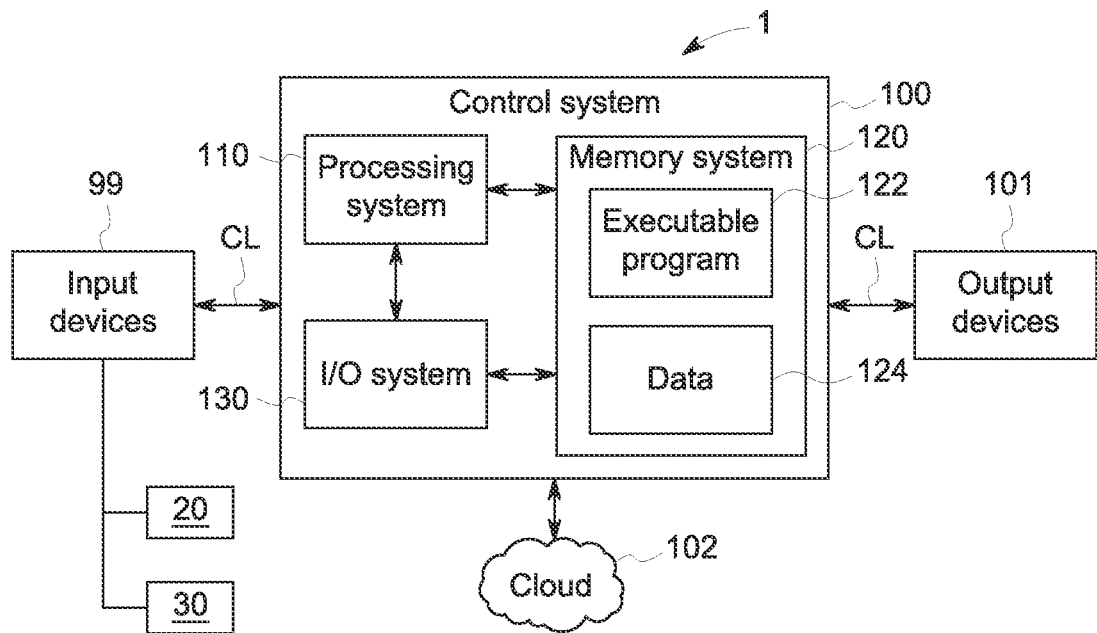
FIG. 9 depicts an exemplary control system for operating the system according to the present disclosure.

FIG. 9 depicts an exemplary overall system 1 as previously described for collecting a biopsy of a lesion within a patient or anatomy 2 based on one or more examination images 50 previously collected from an examination device, which as discussed above may be similar to the biopsy device 30 shown and described above, whereby the lesion 12 has a location along X, Y, and Z axes.

The system 1 includes biopsy device 30 having an x-ray tube 32 configured to emit energy towards the patient or anatomy 2, and an x-ray detector 34 opposite the x-ray tube 32, whereby the x-ray detector 34 is configured to detect the energy emitted towards the patient or anatomy 2 after passing through the patient or anatomy 2. A compression paddle 36 that defines a biopsy window 38 therein is configured to compress the anatomy 2 between the compression paddle 36 and the x-ray detector 34 while the x-rays are emitted from the x-ray tube 32 and detected by the x-ray detector 34.

A processing system 110, which is discussed further below, communicates with a memory system 120 and the x-ray detector 34. The processing system 110 is configured to generate a biopsy image (similar to the images 50 previously shown) of the anatomy 2 based on the x-rays detected by the x-ray detector 34, where this biopsy image includes a depiction of the lesion in image lesion location 13. The processing system 110 is further configured to access the one or more examination images 50 of the anatomy 2 previously collected using the examination device, wherein the images 50 also include lesion in image locations 13. In other words, the lesion 12 may be seen within the images 50. The processing system 110 is further configured to analyze, while the anatomy 2 remains compressed between the compression paddle 36 and the x-ray detector 34 the biopsy image to determine a measured $x_{b-2D}$ coordinate and a measured $y_{b-2D}$ coordinate of the lesion 12 as it appears within the biopsy image along the X and Y axes, respectively. The one or more examination images 50 are then analyzed to determine a measured $z_{b-3D}$ coordinate along the Z axis of the lesion as shown as a lesion in image lesion location 13 within the images 50, which as previously discussed may include a single point or a line of possible locations, for example constituting a segment height SH when the anatomy 2 is segmented into segments 56 within the images 50. Finally, the location of lesion 12 is then determined based on the measured $x_{b-2D}$ coordinate and the measured $y_{b-2D}$ coordinate from biopsy image and the calculated $z_{b-3D}$ coordinate from the one or more examination images 50. The system 1 is then configured for the biopsy at the location determined for the lesion 12 to be performed through the biopsy window 38 of the compression paddle 36 while the anatomy 2 remains compressed between the compression paddle 36 and the x-ray detector 34.

The actual coordinates of the lesion 12 (determined from the measured $x_{b-2D}$ and $y_{b-2D}$ coordinates and the calculated $z_{b-3D}$ coordinate) as positioned within the biopsy device 30 may be provided on a display device (e.g., as an output device 101 in FIG. 9), be provided as a printout, or be shown through other mechanisms presently known in the art, such as that provided by stereo systems today (FIG. 1), for example.

Additional information is now provided for the control system 100 of FIG. 9. Certain aspects of the present disclosure are described or depicted as functional and/or logical block components or processing steps, which may be performed by any number of hardware, software, and/or firmware components configured to perform the specified functions. For example, certain embodiments employ integrated circuit components, such as memory elements, digital signal processing elements, logic elements, look-up tables, or the like, configured to carry out a variety of functions under the control of one or more processors or other control devices. The connections between functional and logical block components are merely exemplary, which may be direct or indirect, and may follow alternate pathways.

In certain examples, the control system 100 communicates with each of the one or more components of the system 1 via a communication link CL, which can be any wired or wireless link. The control system 100 is capable of receiving information and/or controlling one or more operational characteristics of the system 1 and its various sub-systems by sending and receiving control signals via the communication links CL. In one example, the communication link CL is a controller area network (CAN) bus; however, other types of links could be used. It will be recognized that the extent of connections and the communication links CL may in fact be one or more shared connections, or links, among some or all of the components in the system 1. Moreover, the communication link CL lines are meant only to demonstrate that the various control elements are capable of communicating with one another, and do not represent actual wiring connections between the various elements, nor do they represent the only paths of communication between the elements. Additionally, the system 1 may incorporate various types of communication devices and systems, and thus the illustrated communication links CL may in fact represent various different types of wireless and/or wired data communication systems.

The control system 100 may be a computing system that includes a processing system 110, memory system 120, and input/output (I/O) system 130 for communicating with other devices, such as input devices 99 (e.g., an examination device 20 that performed the initial screening and the biopsy device 30) and output devices 101, either of which may also or alternatively be stored in a cloud 102. The processing system 110 loads and executes an executable program 122 from the memory system 120, accesses data 124 stored within the memory system 120, and directs the system 1 to operate as described in further detail below. The system 1 need not include the examination device 20 and/or the biopsy device 30 as inputs, but may instead simply load the images 50 collected therefrom, which may be stored in the memory system 120, for example.

The processing system 110 may be implemented as a single microprocessor or other circuitry, or be distributed across multiple processing devices or sub-systems that cooperate to execute the executable program 122 from the memory system 120. Non-limiting examples of the processing system include general purpose central processing units, application specific processors, and logic devices.

The memory system 120 may comprise any storage media readable by the processing system 110 and capable of storing the executable program 122 and/or data 124. The memory system 120 may be implemented as a single storage device, or be distributed across multiple storage devices or sub-systems that cooperate to store computer readable instructions, data structures, program modules, or other data. The memory system 120 may include volatile and/or non-volatile systems, and may include removable and/or non-removable media implemented in any method or technology for storage of information. The storage media may include non-transitory and/or transitory storage media, including random access memory, read only memory, magnetic discs, optical discs, flash memory, virtual memory, and non-virtual memory, magnetic storage devices, or any other medium which can be used to store information and be accessed by an instruction execution system, for example.

Figure 10:
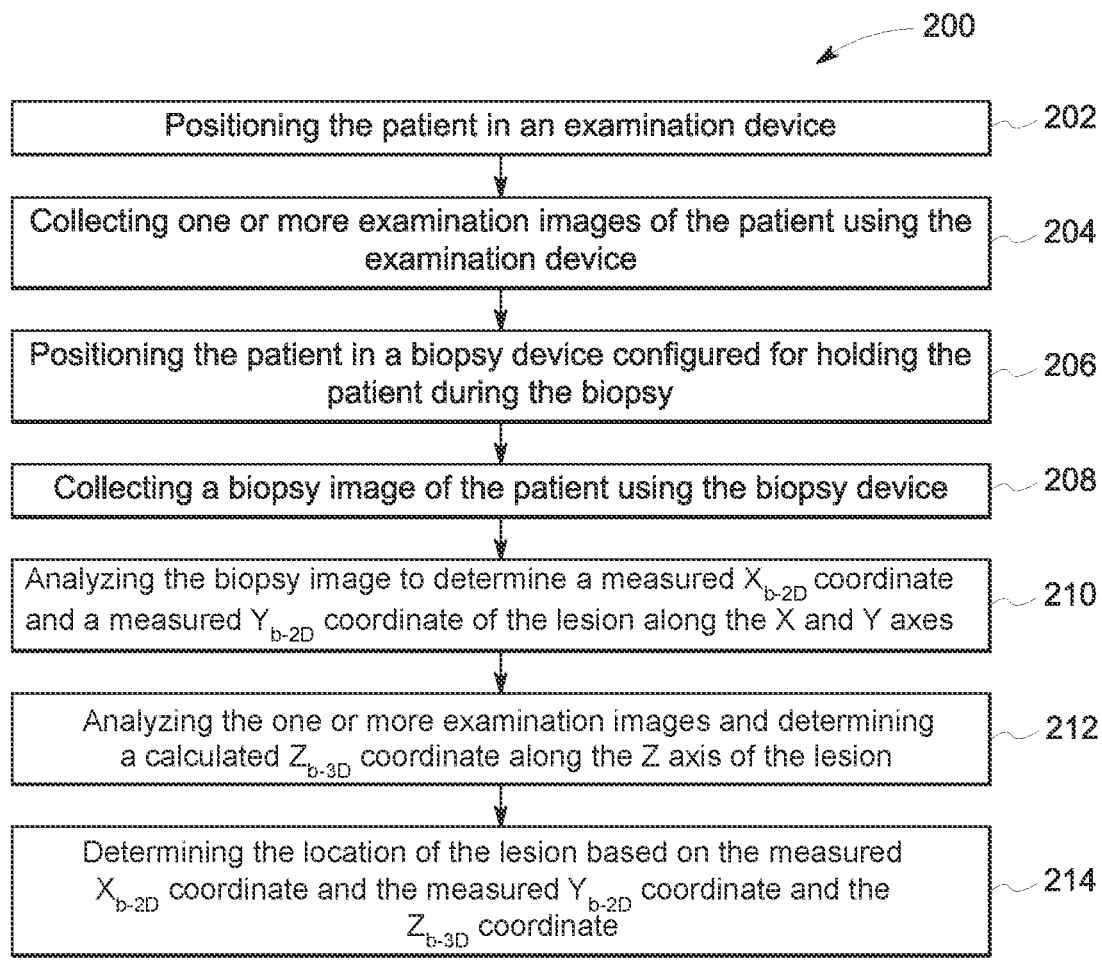
FIG. 10 depicts an exemplary method for determining the location of a lesion for biopsy according to the present disclosure.

As described above and shown in FIG. 10, the present disclosure also relates to a method 200 for determining the location of the lesion of biopsy in a patient or anatomy 2 along X, Y, and Z axes of a detector referential. The method includes positioning the anatomy 2 in an examination device in step 202, which as described above may be an examination device presently known in the art and similar to that shown as the biopsy device 30 and described above. The method includes collecting one or more examination images 50 of the anatomy 2 using the examination device (step 204), where the one or more examination images 50 show the lesion 12 therein. The method includes in step 206 positioning the anatomy 2 in a biopsy device 30 configured for holding the anatomy 2 during the biopsy, then collecting in step 208 a biopsy image of the anatomy 2 using the biopsy device 30, wherein the biopsy image also shows the lesion 12.

The biopsy image is then analyzed in step 210 to determine a measured $x_{b-2D}$ coordinate and measured $y_{b-2D}$ coordinate of the lesion 12 as depicted in the biopsy image along the X and Y axes, respectively. Next, step 212 provides that one or more examination images 50 collected previously with the examination device are analyzed to determine a calculated $z_{b-3D}$ coordinate (or multiple $z_{b-3D}$ coordinates, such as a segment) along the Z axis of the lesion 12 as depicted in the images 50 when the anatomy 2 was positioned within the examination device. Finally, step 214 provides for determining the location of lesion 12 based on the measured $x_{b-2D}$ coordinate and measured $y_{b-2D}$ coordinate from the biopsy image and the calculated $z_{b-3D}$ coordinate from the one or more examination images 50.

The inventors have recognized further benefits for analyzing the pre-existing images from examination devices even in circumstances in which the biopsy device is angulating, such as shown in FIG. 1. With non-angulating biopsy devices, the systems and methods described above provide for calculating or inferring z-plane in which the lesion lies since this information cannot be provided by the single image taken by the biopsy device alone. Angulating biopsy devices do include information for the z-planes of the anatomy of interest, and in fact many "slices" of images in the Z axes that together form a reconstructed view of the anatomy. However, the inventors have recognized that while the $z_{b-3D}$-coordinate of the lesion may thus be identified in this reconstructed volume, it requires a clinician to actually go through the many slices to determine which include the lesion.

As such, the inventors have recognized that the presently disclosed systems and methods can also be used to provide the clinician with an estimate of the z planes of potential interest, saving valuable time and cost when reading 3D volumes from tomosynthesis. In this manner, the presently disclosed systems and methods improve the process of identifying a lesion not only for non-angulating biopsy devices, but also those offering angulation and 3D image acquisitions.

In certain embodiments, the system may go further than indicating to the clinician an estimated $z_{b-3D}$ coordinate for the lesion, such as highlighting or dividing out only the slices of images corresponding to $z_{b-3D}$ coordinates of potential interest. For example, the system may automatically display a subset of images and/or a portion of a reconstructed image corresponding to $z_{b-3D}$ coordinates within a certain percentage of the estimated $z_{b-3D}$ coordinate of the lesion.

The functional block diagrams, operational sequences, and flow diagrams provided in the Figures are representative of exemplary architectures, environments, and methodologies for performing novel aspects of the disclosure. While, for purposes of simplicity of explanation, the methodologies included herein may be in the form of a functional diagram, operational sequence, or flow diagram, and may be described as a series of acts, it is to be understood and appreciated that the methodologies are not limited by the order of acts, as some acts may, in accordance therewith, occur in a different order and/or concurrently with other acts from that shown and described herein. For example, those skilled in the art will understand and appreciate that a methodology can alternatively be represented as a series of interrelated states or events, such as in a state diagram. Moreover, not all acts illustrated in a methodology may be required for a novel implementation.

This written description uses examples to disclose the invention, including the best mode, and also to enable any person skilled in the art to make and use the invention. Certain terms have been used for brevity, clarity, and understanding. No unnecessary limitations are to be inferred therefrom beyond the requirement of the prior art because such terms are used for descriptive purposes only and are intended to be broadly construed. The patentable scope of the invention is defined by the claims and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

What is claimed is:

1. A method for determining a location of a lesion for biopsy in a patient along X, Y, and Z axes, the method comprising:
   receiving the patient in an examination device;
   collecting one or more examination images of the patient using the examination device, wherein the one or more examination images show the lesion;
   releasing the patient from the examination device and receiving the patient in a biopsy device, the biopsy device being configured for holding the patient during the biopsy;

collecting a biopsy image of the patient using the biopsy device, wherein the biopsy image shows the lesion;

analyzing the biopsy image to determine a measured x-coordinate and a measured y-coordinate of the lesion along the X and Y axes, respectively;

analyzing the one or more examination images to determine a calculated z-coordinate of the lesion along the Z axis; and determining the location of the lesion along the X, Y, and Z axes based on the measured x-coordinate and the measured y-coordinate from the biopsy image and the calculated z-coordinate determined from the one or more examination images.

2. The method according to claim 1, wherein the calculated z-coordinate is determined from analysis of at least two of the one or more examination images.

3. The method according to claim 1, further comprising acquiring additional parameters other than from the biopsy image and the one or more examination images, and further comprising including the additional parameters in the analysis of the one or more examination images to determine the calculated z-coordinate of the lesion.

4. The method according to claim 1, wherein the one or more examination images include a first examination image taken in a craniocaudal view and a second examination image taken in one of a mediolateral oblique view and a mediolateral view.

5. The method according to claim 1, wherein the biopsy device is an angulating biopsy device, further comprising displaying the location of the lesion along at least the Z axes.

6. The method according to claim 1, wherein the biopsy image analyzed is exactly one biopsy image, and wherein the exactly one biopsy image is the only image collected of the patient while the patient is positioned in the biopsy device that is analyzed when determining the location of the lesion.

7. The method according to claim 1, wherein the biopsy of the lesion is performable at the location determined by inserting, non-parallel to the Z axes, a needle into the patient.

8. The method according to claim 1, wherein the biopsy image is collected via an x-ray tube of the biopsy device, and wherein the x-ray tube is non-angulating.

9. The method according to claim 1, wherein analyzing the one or more examination images to determine the calculated z-coordinate of the lesion includes identifying one or more landmarks in at least one of the biopsy image and in the one or more examination images.

10. The method according to claim 9, wherein the calculated z-coordinate is determined based on distances between the landmark and the lesion in the first of the one or more examination images.

11. The method according to claim 1, further comprising dividing the one or more examination images into segments, and wherein analyzing the one or more examination images to determine the calculated z-coordinate of the lesion includes identifying which one of the segments the lesion is located in.

12. A method for determining a location of a lesion for biopsy in a patient along X, Y, and Z axes, the method comprising:

positioning the patient in an examination device;

collecting one or more examination images of the patient using the examination device, wherein the one or more examination images show the lesion;

positioning the patient in a biopsy device configured for holding the patient during the biopsy;

collecting a biopsy image of the patient using the biopsy device, wherein the biopsy image shows the lesion;

analyzing the biopsy image to determine a measured x-coordinate and a measured y-coordinate of the lesion along the X and Y axes, respectively;

analyzing the one or more examination images to determine a calculated z-coordinate of the lesion along the Z axis;

determining the location of the lesion along the X, Y, and Z axes based on the measured x-coordinate and the measured y-coordinate from the biopsy image and the calculated z-coordinate determined from the one or more examination images; and dividing the one or more examination images into segments, wherein analyzing the one or more examination images to determine the calculated z-coordinate of the lesion includes identifying which one of the segments the lesion is located in;

wherein the segments are divided as layers between a top and a bottom of the patient stacked along the Z-axis, and wherein the calculated z-coordinate of the location of the lesion is determined based on the one of the segments identified to have the lesion in the one or more examination images.

13. The method according to claim 12, wherein the biopsy is performable using a needle that extends along a longitudinal axis between a tip and a handle, wherein the needle defines a notch therein, wherein the notch has a notch height parallel to the longitudinal axis and the segments have segments heights along the Z-axis, and wherein the notch height is at most equal to the segments heights.

14. The method according to claim 12, wherein the segments include five segments of equal height along the Z-axis.

15. The method according to claim 11, further comprising determining a morphology change to the patient caused by the patient being positioned in the examination device, and wherein determining the calculated z coordinate of the lesion includes analyzing effects of the morphology change in the one or more examination images.

16. A method for determining a location of a lesion for biopsy in a patient along X, Y, and Z axes, the method comprising:

positioning the patient in an examination device;

collecting one or more examination images of the patient using the examination device, wherein the one or more examination images show the lesion;

positioning the patient in a biopsy device configured for holding the patient during the biopsy;

collecting a biopsy image of the patient using the biopsy device, wherein the biopsy image shows the lesion;

analyzing the biopsy image to determine a measured x-coordinate and a measured y-coordinate of the lesion along the X and Y axes, respectively;

analyzing the one or more examination images to determine a calculated z-coordinate of the lesion along the Z axis;

determining the location of the lesion along the X, Y, and Z axes based on the measured x-coordinate and the measured y-coordinate from the biopsy image and the calculated z-coordinate determined from the one or more examination images;

dividing the one or more examination images into segments, wherein analyzing the one or more examination images to determine the calculated z-coordinate of the lesion includes identifying which one of the segments the lesion is located in; and determining a morphology change to the patient caused by the patient being positioned in the examination device, wherein determining the calculated z coordinate of the lesion includes analyzing effects of the morphology change in the one or more examination images;

wherein the segments have segments heights along the Z-axis, and wherein the segment heights are based at least in part on the morphological change determination.

17. The method according to claim 1, wherein at least one of deep learning and artificial intelligence is used for at least one of analyzing the biopsy image to determine the measured x-coordinate and the measured y-coordinate, analyzing the one or more examination images to determine the calculated z-coordinate.

18. The method according to claim 17, further comprising providing training examination images and known z-coordinates of training lesions corresponding thereto to train the at least one of the deep learning and the artificial intelligence.

19. A method for determining a location of a lesion for biopsy in a patient along X, Y, and Z axes, the method comprising:

receiving the patient in an examination device;

collecting one or more examination images of the patient using the examination device, wherein the one or more examination images show the lesion;

receiving the patient in a biopsy device configured for holding the patient during the biopsy;

collecting a biopsy image of the patient using the biopsy device, wherein the biopsy image shows the lesion;

analyzing the biopsy image to determine a measured x-coordinate and a measured y-coordinate of the lesion along the X and Y axes, respectively;

analyzing the one or more examination images to determine a calculated z-coordinate of the lesion along the Z axis; and determining the location of the lesion along the X, Y, and Z axes based on the measured x-coordinate and the measured y-coordinate from the biopsy image and the calculated z-coordinate determined from the one or more examination images;

wherein at least one of deep learning and artificial intelligence is used for at least one of analyzing the biopsy image to determine the measured x-coordinate and the measured y-coordinate, analyzing the one or more examination images to determine the calculated z-coordinate; and wherein the at least one of the deep learning and the artificial intelligence applies a biomechanical model.

* * * * *